United States Patent [19]

Decoster et al.

[11] Patent Number: 6,150,311

[45] Date of Patent: Nov. 21, 2000

[54] DETERGENT COSMETIC COMPOSITIONS AND THEIR USE

[75] Inventors: Sandrine Decoster, Epinay sur Seine; Bernard Beauquey, Clichy, both of France

[73] Assignee: L'Oreal, Paris, France

[21] Appl. No.: 09/333,006

[22] Filed: Jun. 15, 1999

[30] Foreign Application Priority Data

Jun. 16, 1998 [FR] France .................................. 98 07583

[51] Int. Cl.⁷ ............................ A61K 7/045; A61K 7/50; C11D 3/38
[52] U.S. Cl. .......................... 510/122; 510/123; 510/158; 510/466
[58] Field of Search .................... 510/122, 123, 510/124, 158, 466

[56] References Cited

U.S. PATENT DOCUMENTS

| | | |
|---|---|---|
| 2,528,378 | 10/1950 | Mannheimer . |
| 2,781,354 | 2/1957 | Mannheimer . |
| 4,431,789 | 2/1984 | Okazaki et al. . |
| 5,180,584 | 1/1993 | Sebag et al. .............................. 424/401 |
| 5,275,755 | 1/1994 | Sebag et al. .......................... 252/174.15 |
| 5,476,649 | 12/1995 | Naito et al. .............................. 424/70.1 |
| 5,536,493 | 7/1996 | Dubief .................................. 424/70.13 |
| 5,627,148 | 5/1997 | Dubief et al. ............................. 510/122 |
| 5,690,920 | 11/1997 | Dubief .................................. 424/70.12 |
| 5,705,147 | 1/1998 | Shapiro et al. .......................... 424/70.1 |
| 5,858,341 | 1/1999 | Beauquey et al. ..................... 424/70.19 |
| 6,022,836 | 2/2000 | Dubief et al. ............................. 510/122 |
| 6,028,041 | 2/2000 | Decoster et al. .......................... 510/119 |

FOREIGN PATENT DOCUMENTS

| | | |
|---|---|---|
| 0 337 354 | 10/1989 | European Pat. Off. . |
| 2 470 596 | 6/1981 | France . |
| 2 519 863 | 7/1983 | France . |
| 2 598 611 | 11/1987 | France . |
| 62-34039 | 7/1987 | Japan . |
| 4-020053 | 1/1992 | Japan . |
| 9-71504 | 3/1997 | Japan . |
| 10-316527 | 12/1998 | Japan . |
| 10-316540 | 12/1998 | Japan . |

OTHER PUBLICATIONS

M.R. Porter, "Handbook of Surfactants", Blackie & Son (Glasgow and London), 1991, pp. 116–178.
Patent Abstracts of Japan, vol. 018, No. 482, Sep. 8, 1994 (JP 06 157236).
Derwent Publications Ltd., London, Class A26, AN 95–167159, Apr. 4, 1995 (JP 07 089825).
Patent Abstracts of Japan, vol. 098, No. 002, Jan. 30, 1998 (JP 09 278892).
Patent Abstracts of Japan, vol. 097, No. 007, Jul. 31, 1997 (JP 09 071504).
English language Derwent Abstract of FR 2 598 611.
English language Derwent Abstract of FR 2 470 596.
English language Derwent Abstract of FR 2 519 863.
English language Derwent Abstact of JP 09–071504.
Patent Abstracts of Japan for JP 10–316527.
Patent Abstracts of Japan for JP 10–316540.
Patent Abstracts of Japan for JP 57–14920.

*Primary Examiner*—Yogendra Gupta
*Assistant Examiner*—John M Petruncio
*Attorney, Agent, or Firm*—Finnegan, Henderson, Farabow, Garrett & Dunner, L.L.P

[57] ABSTRACT

The invention relates to conditioning and detergent compositions comprising, in a cosmetically acceptable medium, (A) a washing base and (B) at least one silicone comprising at least one glycerol group. The compositions can be applied for the cleansing and care of the hair or skin.

33 Claims, No Drawings

DETERGENT COSMETIC COMPOSITIONS AND THEIR USE

The present invention relates to novel cosmetic compositions having improved properties which are intended simultaneously for the cleansing and the conditioning of keratinous materials such as the hair and which comprise, in a cosmetically acceptable aqueous vehicle, a washing base which comprises detersive surfactants and which also comprises, by way of conditioners, a silicone which is soluble in water and has a glycerol group. The invention also relates to the use of the compositions in the above-mentioned cosmetic application.

For the cleansing and/or washing of keratinous matter such as the hair, it is common to use detergent compositions (such as shampoos) based essentially on conventional surfactants of, in particular, anionic, nonionic and/or amphoteric type, but more particularly of anionic type. These compositions are applied to wetted hair and the foam generated by massage or friction with the hands makes it possible, after rinsing with water, to remove the various types of dirt present initially on the hair.

These base compositions do indeed possess a good washing power, but the intrinsic cosmetic properties associated with them remain fairly weak, in particular owing to the fact that the relatively aggressive nature of such a cleansing treatment may in the long term cause more or less marked damage to the hair fibre, this damage being associated in particular with the progressive removal of the lipids or proteins contained in or on the surface of the said fibre.

Furthermore, to improve the cosmetic properties of the above detergent compositions, and more particularly of those which are intended for application to sensitized hair (that is, hair which is damaged or weakened, especially as a result of the chemical action of atmospheric agents and/or of hair treatments such as permanent-waving, dyeing or bleaching), it is now customary to introduce complementary cosmetic agents into such compositions, these complementary agents being referred to as conditioners and being intended primarily to repair or to limit the harmful or undesirable effects induced by the various treatments or attacks which the hair fibres undergo to a more or less repeated extent. These conditioners may of course also improve the cosmetic behaviour of the natural hair.

With this aim in mind it has already been proposed to use silicones and, more particularly, insoluble silicones. In fact, hitherto, in order to attain a deposit of silicone on the keratinous matter in the course of rinsing, use has been made of insoluble silicones. Insoluble compounds, and more particularly silicones, have the disadvantage of being difficult to maintain in uniform dispersion in the medium.

The silicones must also be transported onto the keratinous matter that is treated with the aim of imparting to it, following application, properties of softness, shine and disentanglement without inducing any greasiness.

Therefore, following major research carried out into this question, the inventors have now found that, by using a washing base and at least one silicone containing at least one glycerol group, which is soluble in the composition, it is possible to obtain stable detergent compositions having excellent cosmetic properties, in particular: ease of styling, form retention, suppleness and volume in the hair treated, and having good service properties, such as good intrinsic washing power and good foaming power.

Industrial implementation is extremely easy, and the cosmetic properties of the shampoos can be markedly superior to those of shampoos containing soluble silicones such as silicones having one or more ethoxylated groups.

The compositions according to the invention impart to the hair, after rinsing, a notable treatment effect which is manifested, in particular, by ease of disentangling, as well as providing body, lightness, smoothness, softness and suppleness without any greasy sensation.

The present invention therefore provides novel conditioning and detergent cosmetic compositions, characterized in that they comprise, in a cosmetically acceptable aqueous medium, (A) a washing base and (B) at least one silicone comprising at least one glycerol group and not containing a carboxylic ester function.

The invention additionally provides for the use in cosmetology of the above compositions for the cleansing and/or removal of make-up from and/or conditioning of keratinous matter such as the hair and skin.

A—Washing Base:

The compositions according to the invention necessarily include a washing base, which is generally aqueous.

The surfactant or surfactants forming the washing base can be selected arbitrarily, alone or in a mixture, from anionic, amphoteric, nonionic and cationic surfactants.

However, according to the invention, the washing base preferably comprises anionic surfactants or mixtures of anionic surfactants and amphoteric surfactants or nonionic surfactants.

Therefore, in accordance with the invention, the washing base can preferably represent from 4 to 50% by weight, more preferably from 6 to 35% by weight and, most preferably, from 8 to 25% by weight of the total weight of the final composition.

The surfactants suitable for the implementation of the present invention are, in particular, as follows:

(i) Anionic surfactant(s):

Within the scope of the present invention, the nature of these surfactants is not truly critical.

Thus, by way of example of anionic surfactants which can be used, alone or in a mixture, in the context of the present invention, mention may be made in particular (non-limitative list) of the salts (in particular alkali metal salts, especially sodium salts, ammonium salts, amine salts, amino alcohol salts or magnesium salts) of the following compounds: alkyl sulphates, alkyl ether sulphates, alkylamido ether sulphates, alkylaryl polyether sulphates, monoglyceride sulphates; alkylsulphonates, alkyl phosphates, alkylamidesulphonates, alkylarylsulphonates, α-olefinsulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acylsarcosinates; acylisethionates and N-acyltaurates, the alkyl or acyl radical of all these various compounds preferably containing 12 to 20 carbon atoms, and the aryl radical denoting preferably a phenyl or benzyl group. Among the anionic surfactants which can also be used mention may also be made of the salts of fatty acids such as the salts of oleic, ricinoleic, palmitic and stearic acid, the acids of copra oil or hydrogenated copra oil; and the acyl-lactylates whose acyl radical contains 8 to 20 carbon atoms. It is also possible to use weakly anionic surfactants, such as alkyl-D-galactosideuronic acids and their salts and also polyalkoxylated alkyl ($C_6$–$C_{24}$) ether carboxylic acids, polyalkoxylated alkyl ($C_6$–$C_{24}$)-aryl ether carboxylic acids, polyalkoxylated alkyl ($C_6$–$C_{24}$)-amido ether carboxylic acids and their salts, especially those containing 2 to 50 ethylene oxide groups, and mixtures thereof.

Among the anionic surfactants, preference will be given, in accordance with the invention, to the use of the salts of alkyl sulphates and of alkyl ether sulphates and mixtures thereof.

(ii) Nonionic surfactant(s):

The nonionic surfactants are also compounds which are well known per se (in this regard see, in particular "Handbook of Surfactants" by M.R. Porter, Blackie & Son (Glasgow and London), 1991, pp. 116–178, the disclosure of which is specifically incorporated by reference herein) and whose nature, within the scope of the present invention, is not critical. Therefore, they can be selected in particular (non-limitative list) from alcohols, alpha-diols, alkylphenols or polyethoxylated, polypropoxylated or polyglycerolated fatty acids having a fatty chain containing for example 8 to 18 carbon atoms, it being possible for the number of ethylene oxide or propylene oxide groups to range, in particular, from 2 to 50 and for the number of glycerol groups to range, in particular, from 2 to 30. Mention may also be made of ethylene oxide and propylene oxide copolymers, the condensates of ethylene oxide and propylene oxide with fatty alcohols; polyethoxylated fatty amides having preferably from 2 to 30 mols of ethylene oxide, polyglycerolated fatty amides containing on average from 1 to 5 glycerol groups and in particular from 1.5 to 4; polyethoxylated fatty amines having preferably 2 to 30 mols of ethylene oxide; ethoxylated sorbitan fatty acid esters having 2 to 30 mols of ethylene oxide; sucrose fatty acid esters, polyethylene glycol fatty acid esters, alkylpolyglycosides, N-alkylglucamine derivatives, amine oxides, such as ($C_{10}$–$C_{14}$)-alkylamine oxides or N-acylaminopropylmorpholine oxides. It will be noted that the alkylpolyglycosides constitute nonionic surfactants which enter particularly well into the scope of the present invention.

(iii) Amphoteric surfactant(s):

The amphoteric surfactants, the nature of which does not assume any critical character in the context of the present invention, may in particular (non-limitative list) be derivatives of aliphatic secondary or tertiary amines in which the aliphatic radical is a linear or branched chain containing 8 to 22 carbon atoms and containing at least one water-solubilizing anionic group (for example carboxylate, sulphonate, sulphate, phosphate or phosphonate); mention may also be made of alkyl($C_8$–$C_{20}$)betaines, sulphobetaines, alkyl($C_8$–$C_{20}$)-amidoalkyl($C_1$–$C_6$)betaines or alkyl($C_8$–$C_{20}$) amidoalkyl($C_1$–$C_6$)sulphobetaines.

Among the amine derivatives, mention may be made of the products sold under the name MIRANOL®, as are described in the U.S. Pat. Nos. 2,528,378 and 2,781,354, the disclosure of each of which is specifically incorporated by reference herein, with structures:

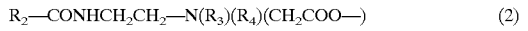

$$R_2\text{—CONHCH}_2\text{CH}_2\text{—N}(R_3)(R_4)(\text{CH}_2\text{COO—}) \quad (2)$$

in which: $R_2$ is chosen from alkyl radicals derived from $R_2$—COOH acids present in hydrolysed copra oil, heptyl, nonyl and undecyl radicals, $R_3$ denotes a beta-hydroxyethyl group and $R_4$ denotes a carboxymethyl group; and

$$R_2\text{—CONHCH}_2\text{CH}_2\text{—N(B)(C)} \quad (3)$$

in which:

B represents —$CH_2CH_2OX'$, C represents —$(CH_2)_z$—Y', where z=1 or 2,

X' is chosen from the —$CH_2CH_2$—COOH radical and a hydrogen atom,

Y' is chosen from —COOH and the radical —$CH_2$—CHOH—$SO_3H$, and $R_2$ is chosen from alkyl radicals $R_9$ of $R_9$—COOH acids present in oils chosen from copra oil and hydrolysed linseed oil, an alkyl radical, in particular $C_7$, $C_9$, $C_{11}$ or $C_{13}$, $C_{17}$ alkyl radicals and isoforms thereof, and unsaturated $C_{17}$ radicals.

These compounds are classified in the CTFA dictionary, $5^{th}$ Edition, 1993, under the names Disodium Cocoamphodiacetate, Disodium Lauroamphodiacetate, Disodium Caprylamphodiacetate, Disodium Capryloamphodiacetate, Disodium Cocciamphodipropionate, Disodium Lauroamphodipropionate, Disodium Caprylamphodipropionate, Disodium Caproyloamphodipropionate, Lauroamphodipropionic acid and Cocoamphodipropionic acid. By way of example, mention may be made of the cocoamphodiacetate sold under the trade name MIRANOL® C2M by the company RHONE-POULENC.

In the compositions according to the invention, it is preferred to use mixtures of surfactants and, in particular, mixtures of anionic surfactants and amphoteric or nonionic surfactants. A particularly preferred mixture is a mixture containing at least one anionic surfactant and at least one amphoteric surfactant.

Preferably, use is made of at least one anionic surfactant, including mixtures of course, chosen from ammonium, triethanolamine and sodium ($C_{12}$–$C_{14}$)alkyl sulphates, sodium ($C_{12}$–$C_{14}$)alkyl ether sulphates ethoxylated with 2.2 mols of ethylene oxide, sodium cocoylisethionate and sodium alpha-($C_{14}$–$C_{16}$)olefin sulphonate, with:

either an amphoteric surfactant such as the amine derivatives known as disodium cocoamphodipropionate or sodium cocoamphopropionate, which are sold in particular by the company RHONE-POULENC under the trade name "MIRANOL® C2M CONC" as an aqueous solution containing 38% of active substance or under the name MIRANOL® C32;

or an amphoteric surfactant of zwitterionic type such as alkyl betaines, in particular the cocoyl betaine sold under the name "DEHYTON® AB 30" as an aqueous solution containing 32% of a.s. by the company HENKEL or the alkylamido betaines such as TEGOBetaineE® F50 sold by the company GOLDSCHMIDT.

(iv) Cationic surfactants:

Representative cationic surfactants include (non-limitative list): the salts of optionally polyoxyalkylenated primary, secondary or tertiary fatty amines; quaternary ammonium salts, such as tetraalkylammonium, alkylamidoalkyltrialkylammonium, trialkylbenzylammonium, trialkylhydroxyalkylammonium or alkylpyridinium bromides or chlorides; imidazoline derivatives; or amine oxides which are cationic in nature. It will be noted that the cationic surfactants do not constitute preferred surfactants for the implementation of the present invention, but the use thereof is not ruled out.

B—Glycerol-functional Silicone

The compositions according to the invention necessarily include a silicone containing at least one glycerol group, which is soluble in the composition and which does not contain a carboxylic ester function.

The silicones comprising at least one glycerol group are selected, for example, from the compounds of general formulae (I) and (II):

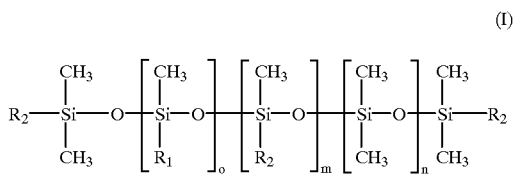

(I)

-continued

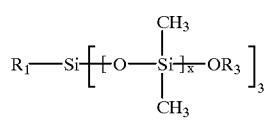 (II)

in which:
$R_1$, which is identical or different, is chosen from saturated and unsaturated linear and branched $C_1$–$C_{30}$ alkyl radicals and phenyl,
$R_2$, which is identical or different, is chosen from a radical selected from:
$R_1$,

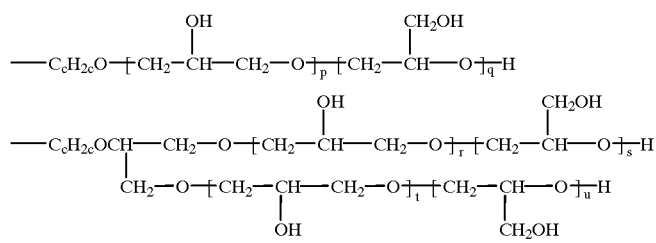

$R_3$, which is identical or different, represents a radical selected from:

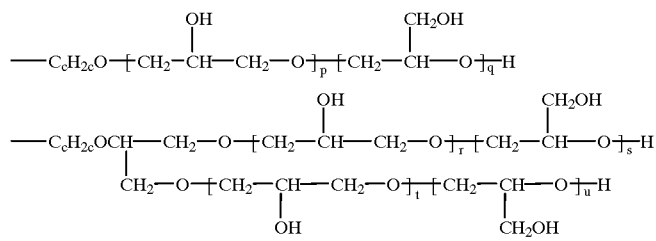

c can vary from 1 to 10,
m cain vary from 1 to 50,
n can vary from 0 to 500,
o can vary from 0 to 20,
p can vary from 0 to 50,
q can vary from 0 to 50,
p+q is greater than or equal to 1 and is preferably lower than 100,
r cain vary from 0 to 50,
s can vary from 0 to 50,
r+s is greater than or equal to 1 and is preferably lower than 100,
t can vary from 0 to 50,
u can vary from 0 to 50,
t+u is greater than or equal to 1 and is preferably lower than 100, and
x can vary from 1 to 100,
with the proviso that at least one radical $R_2$ does not denote $R_1$.

More particularly, these formulae meet at least one, and preferably all, of the following conditions:
$R_1$ denotes the methyl radical.

$R_2$ denotes:

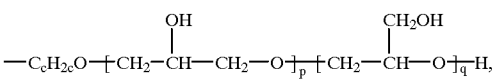

c is equal to 2 or 3.
q varies from 0 to 20, preferably from 0 to 10.
p varies from 0 to 20, preferably from 0 to 10.
p+q varies from 1 to 10.

Preferably, use is made of the glycerol silicones corresponding to the general formula (I).

The silicones according to the invention are, for example, polydimethylsiloxanes having at least one group of formula (A) or (B)

—$CH_2$—$CH_2$—$CH_2$—O—($CH_2$—$CH(CH_2OH)$—O$)_p$—H (A)
—$CH_2$—$CH_2$—$CH_2$—O—$CH_2$—$CH(OH)$—$CH_2$—O—($CH_2$—
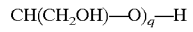
$CH(CH_2OH)$—O$)_q$—H (B)

in which p and q are numbers preferably between 1 and 50, more particularly between 1 and 10.

Silicones of this kind are described in particular in the U.S. Pat. No. 4,431,789 and in the Application JP09 071504, the disclosures of which are specifically incorporated by reference herein.

Products which are particularly suitable for the realization of the invention are, for example, the polydimethylsiloxanes having triglycerol groups which are provided by SHIN-ETSU under the names X224947, X22-6147 and X22-6148.

The silicone or silicones can preferably be used in the compositions according to the invention in concentrations which are generally from 0.1 to 15% and, more preferably, from 0.2 to 10% by weight relative to the total weight of the composition, and even more preferably from 0.5 to 5% by weight.

The cosmetically acceptable aqueous medium may consist solely of water or comprise a mixture of water and a cosmetically acceptable solvent such as a $C_1$–$C_4$ lower alcohol, such as ethanol, isopropanol, tert-butanol or n-butanol; alkylene glycols, 5 such as propylene glycol, and glycol ethers.

The detergent compositions according to the invention have a final pH which is generally from 3 to 10. Preferably, this pH is from 5 to 8. The adjustment of the pH to the desired value can be done conventionally by adding a base (organic or inorganic) to the composition, for example aqueous ammonia or a primary, secondary or tertiary (poly) amine, such as monoethanolamine, diethanolamine, triethanolamine, isopropanolamine or 1,3-propanediamine, or else by adding an acid, preferably a carboxylic acid such as, for example, citric acid.

The compositions according to the invention can comprise, in addition to the above(-defined combination, viscosity regulators, such as electrolytes, or thickeners. Mention may be made in particular of sodium chloride, sodium xylenesulphonate, scleroglucans, xanthane gums, fatty acid alkanolamides, alkyl ether carboxylic acid alkanolamides, optionally ethoxylated with up to 5 mols of ethylene oxide, such as the product sold under the name "AMINOL A15" by the company CHEM Y, crosslinked polyacrylic acids and crosslinked $C_{10}$–$C_{30}$ alkyl acrylate-acrylic acid copolymers. These viscosity regulators are used in compositions according to the invention in proportions which can range up to 10% by weight relative to the total weight of the composition.

The compositions according to the invention may additionally comprise, preferably up to 5%, pearlizing or opacifying agents which are well known in the prior art, such as, for example, fatty alcohols higher than C16, sodium or magnesium palmitates, sodium or magnesium hydroxystearates and stearates, fatty alcohols, or fatty chain acylated derivatives, such as ethylene glycol or polyethylene glycol monostearates or distearates, and fatty chain ethers such as, for example, distearyl ether or 1-(hexadecyloxy)-2-octadecanol.

The compositions according to the invention may additionally comprise other agents having the effect of improving the cosmetic properties of hair or of the skin without, however, impairing the stability of the compositions. In this respect, mention may be made of cationic surfactants, anionic or nonionic or cationic or amphoteric polymers, proteins, protein hydrolysates, ceramides, pseudoceramides, $C_{16}$–$C_{40}$ linear or branched-chain fatty acids such as 18-methyleicosanoic acid, hydroxy acids, vitamins, panthenol, volatile or non-volatile silicones other than the silicones of the invention, the agents being soluble or insoluble in the medium, and mixtures of the agents.

The cationic polymer conditioners which can be used in accordance with the present invention can be selected from among all those which are already known per se as improving the cosmetic properties of the hair treated by detergent compositions, namely, in particular, those described in the Patent Application EP-A-0 337 354 and in the French Patent Applications FR-A-2 270 846, 2 383 660, 2 598 611, 2 470 596 and 2 519 863, the disclosures of all of which are specifically incorporated by reference herein.

Still more generally, within the meaning of the present invention, the expression "cationic polymer" denotes any polymer containing cationic groups and/or groups which can be ionized to cationic groups.

Among all the cationic polymers which may be used in the context of the present invention, preference will be given to employing quaternary cellulose ether derivatives such as the products sold under the name "JR 400" by the company UNION CARBIDE CORPORATION, cyclopolymers, in particular diallyldimethylammonium salt homopolymers and copolymers of diallyldimethylammonium salt and acrylamide, especially the chlorides, which are sold under the names "MERQUAT 100", "MERQUAT 550" and "MERQUAT S" by the company MERCK, cationic polysaccharides and, more particularly, guar gums modified by 2,3-epoxypropyltrimethylammonium chloride, which are sold, for example, under the name "JAGUAR C13S" by the company MEYHALL.

According to the invention, the cationic polymer or polymers may preferably represent from 0.001 to 10% by weight, more preferably from 0.005 to 5% by weight and, even more preferably, from 0.01 to 3% by weight of the total weight of the final composition.

The compositions according to the invention may also comprise foam synergists, such as $C_{10}$–$C_{18}$ 1,2-alkanediols or fatty alkanolamides derived from monoethanolamine or diethanolamine.

Of course, the person skilled in the art will take care to select the possible additional compound(s) and/or its (their) amounts such that the advantageous properties intrinsically linked to the combination (washing base+glycerol silicone) in accordance with the invention are not, or not substantially, impaired by the envisaged addition or additions.

These compositions can be provided in the form of more or less thickened liquids, creams or gels, and are primarily suitable for washing and caring for keratinous matter, in particular the hair and skin and, more particularly, the hair.

When the compositions according to the invention are employed as conventional shampoos, they are simply applied to wetted hair and the foam generated by massage or friction with the hands is subsequently removed, after an optional waiting time, by rinsing with water, it being possible to repeat this operation one or more times.

The invention additionally provides a method of washing and conditioning keratinous matter such as, in particular, the hair, which comprises applying to the said wetted matter an effective amount of a composition as defined above and then carrying out rinsing with water after an optional waiting time.

The compositions according to the invention are preferably used as shampoos for the washing and conditioning of hair, and in the latter case they are applied to wet hair in amounts which are effective for washing the said hair, this application being followed by rinsing with water.

The compositions according to the invention can also be used as shower gels for washing and conditioning the hair and/or skin, in which case they are applied to the wet skin and/or hair and are rinsed off after application.

Specific but by no means limiting examples illustrating the invention will now be given.

EXAMPLE

Two shampoo compositions were formulated, one in accordance with the invention (composition A) and the other comparative (composition B):

| | A Invention | B Comparative |
|---|---|---|
| Sodium lauryl ether sulphate (70/30 C12/C14) containing 2.2 mol of ethylene oxide, as an aqueous solution with an a.s. content of 28% (a.s. = active substance) | 15 ga.s. | 15 ga.s. |
| Cocoyl betaine (DEHYTON AB 30) | 2.7 ga.s. | 2.7 ga.s. |
| Triglycerol silicone (*) | 2.7 g | — |
| Ethoxylated silicone (**) | — | 2.7 g |
| Cationic guar gum | 0.05 g | 0.05 g |
| Mixture of cetyl alcohol and 1-(hexadecyloxy)-2- | 2.5 g | 2.5 g |

|                              | A Invention | B Comparative |
|------------------------------|-------------|---------------|
| octadecanol                  |             |               |
| Copra acid monoisopropanolamide | 1 g      | 1 g           |
| Perfume, preservative        | q.s.        | q.s.          |
| Citric acid q.s. pH          | 7.6         | 7.6           |
| Demineralized water q.s.     | 100 g       | 100 g         |

(*) Triglycerol silicone: Polydimethylsiloxane with triglycerol groups, sold by the company SHIN-ETSU under the name X22 4947.
(**) Ethoxylated silicone: Polydimethylsiloxane containing oxyethylene groups, sold by the company DOW CORNING under the name DC193.

(*)Triglycerol silicone: Polydimethylsiloxane with triglycerol groups, sold by the company SHIN-ETSU under the name X22 4947.

(**) Ethoxylated silicone: Polydimethylsiloxane containing oxyethylene groups, sold by the (company DOW CORNING under the name DC193.

Shampooing was carried out by applying approximately 12 g of composition A to sensitized hair which had been wetted beforehand. The shampoo is foamed, and then thorough rinsing is carried out with water.

The same procedure as above is followed with the comparative composition B.

A panel of experts evaluated the appearance of the hair.

All of the experts indicated that the hair treated with composition A according to the invention is softer and smoother than the hair treated with composition B.

What is claimed is:

1. A conditioning and detergent cosmetic composition comprising:

(A) a washing base and (B) at least one silicone having at least one glycerol group and not containing a carboxylic ester function.

2. The composition according to claim 1, wherein said washing base comprises at least one surfactant chosen from anionic, amphoteric, nonionic and cationic surfactants.

3. The composition according to claim 1, wherein said washing base is present in an amount from 4 to 50% by weight relative to the total weight of the composition.

4. The composition according to claim 3, wherein said washing base is present in an amount from 6 to 35% by weight relative to the total weight of the composition.

5. The composition according to claim 4, wherein said washing base is present in an amount from 8 to 25% by weight relative to the total weight of the composition.

6. The composition according to claim 1, wherein said at least one silicone having at least one glycerol group is chosen from silicones of formulae (I) and (II):

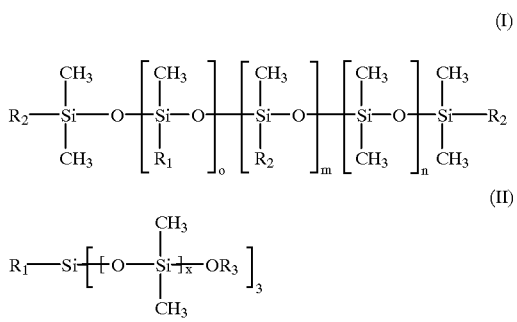

in which:

$R_1$, which is identical or different, is chosen from saturated and unsaturated, linear and branched, $C_1$–$C_{30}$ alkyl radicals and phenyl, $R_2$, which is identical or different, is chosen from:

$R_1$,

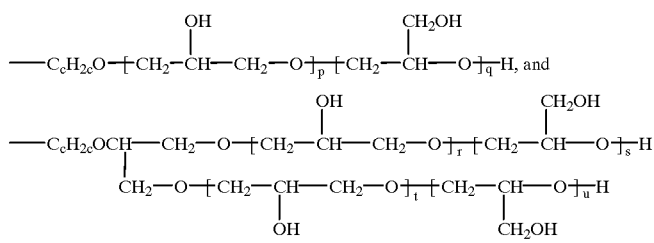

$R_3$, which is identical or different, is chosen from:

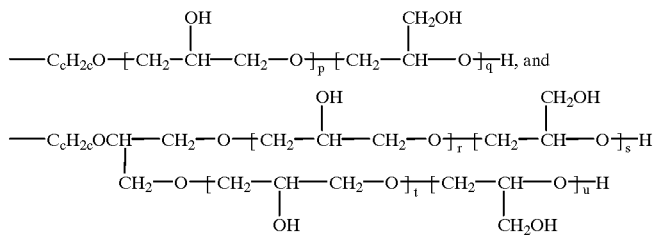

c varies from 1 to 10,
m varies from 1 to 50,
n varies from 0 to 500,
o varies from 0 to 20,
p varies from 0 to 50,
q varies from 0 to 50, p+q is greater than or equal to 1,
r varies from 0 to 50,
s varies from 0 to 50,
r+s is greater than or equal to 1,
t varies from 0 to 50,
u varies from 0 to 50,
t+u is greater than or equal to 1, and
x varies from 1 to 100, with the proviso that at least one radical $R_2$ does not denote $R_1$.

7. The composition according to claim 6, wherein said silicones of the formula (I) and (II) meet at least one of the following conditions:

$R_1$ denotes the methyl radical, $R_2$ denotes:

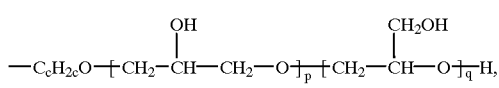

c is equal to 2 or 3,
q varies from 0 to 20,
p varies from 0 to 20,
p+q varies from 1 to 10.

8. The composition according to claim 7, wherein
q varies from 0 to 10,
p varies from 0 to 10.

9. The composition according to claim 6, wherein said silicones of the formula (I) and (II) meet all of the following conditions:

$R_1$ denotes the methyl radical, $R_2$ denotes:

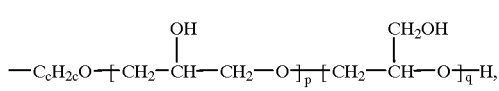

c is equal to 2 or 3,
q varies from 0 to 20,
p varies from 0 to 20,
p+q varies from 1 to 10.

10. The composition according to claim 9, wherein
q varies from 0 to 10,
p varies from 0 to 10.

11. The composition according to claim 6, wherein said at least one silicone having at least one glycerol group is chosen from compounds of formula (I).

12. The composition according to claim 7, wherein said silicones are of formula (I).

13. The composition according to claim 9, wherein said silicones are of formula (I).

14. The composition according to claim 1, wherein said at least one silicone having at least one glycerol group is chosen from polydimethylsiloxanes having at least one group of formula (A) or (B)

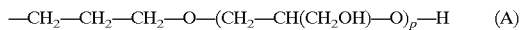

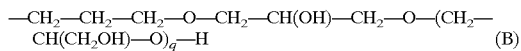

in which p and q are numbers ranging from 1 to 10.

15. The composition according to claim 1, wherein said at least one silicone having at least one glycerol group is present in concentrations ranging from 0.1 to 15% by weight relative to the total weight of the composition.

16. The composition according to claim 15, wherein said at least one silicone having at least one glycerol group is present in concentrations ranging from 2 to 10% by weight relative to the total weight of the composition.

17. The composition according to claim 1, further comprising at least one adjuvant chosen from cationic surfactants, anionic, nonionic, cationic, and amphoteric polymers, proteins, ceramides, pseudoceramides and silicones.

18. The composition according to claim 17, wherein said cationic polymers are chosen from quaternary cellulose ethers, diallyldimethylammonium salt homopolymers, diallyidimethylammonium salt-acrylamide copolymers, and cationic polysaccharides.

19. The composition according to claim 18, wherein said at least one adjuvant is chosen from cationic polymers representing from 0.001 to 10% by weight of the total weight of the composition.

20. The composition according to claim 19, wherein said at least one adjuvant is chosen from cationic polymers representing from 0.005 to 5% by weight of the total weight of the composition.

21. The composition according to claim 20, wherein said at least one adjuvant is chosen from cationic polymers representing from 0.01 to 3% by weight of the total weight of the composition.

22. A method for cleansing and/or conditioning keratinous matter comprising applying to said keratinous matter an effective amount of a composition, said composition comprising:
(A) a washing base and
(B) at least one silicone having at least one glycerol group and not containing a carboxylic ester function.

23. A method for cleansing and/or removal of make-up from keratinous matter comprising applying to said keratinous matter an effective amount of a composition, said composition comprising:
(A) a washing base and
(B) at least one silicone having at least one glycerol group and not containing a carboxylic ester function.

24. A method for washing and conditioning keratinous matter comprising applying an effective amount of a composition to wetted keratinous matter, and rinsing with water, said composition comprising:
(A) a washing base and
(B) at least one silicone having at least one glycerol group and not containing a carboxylic ester function.

25. The method according to claim 24, wherein said keratinous matter is hair.

26. The method according to claim 25, wherein said hair is human hair.

27. The method according to claim 26, wherein said rinsing occurs after a waiting time.

28. A shampoo comprising:
(A) a washing base and
(B) at least one silicone having at least one glycerol group and not containing a carboxylic ester function.

29. A shower gel comprising
(A) a washing base and
(B) at least one silicone having at least one glycerol group and not containing a carboxylic ester function.

30. The method according to claim 22, wherein said keratinous matter is hair.

31. The method according to claim 30, wherein said hair is human hair.

32. The method according to claim 23, wherein said keratinous matter is hair.

33. The method according to claim 32, wherein said hair is human hair.

* * * * *